United States Patent
Pirker

(10) Patent No.: US 8,287,279 B2
(45) Date of Patent: Oct. 16, 2012

(54) TOOTH IMPLANT

(75) Inventor: Wofgang Pirker, Vienna (AT)

(73) Assignee: Wolfgang Pirker, Vienna (AT)

( * ) Notice: Subject to any disclaimer, the term of this patent is extended or adjusted under 35 U.S.C. 154(b) by 154 days.

(21) Appl. No.: 12/089,268

(22) PCT Filed: Oct. 5, 2006

(86) PCT No.: PCT/AT2006/000405
§ 371 (c)(1),
(2), (4) Date: Apr. 4, 2008

(87) PCT Pub. No.: WO2007/038817
PCT Pub. Date: Apr. 12, 2007

(65) Prior Publication Data
US 2009/0092944 A1    Apr. 9, 2009

(30) Foreign Application Priority Data
Oct. 5, 2005    (AT) .................... 1628/2005

(51) Int. Cl.
*A61C 8/00* (2006.01)
(52) U.S. Cl. .............. 433/175; 433/173; 433/201.1
(58) Field of Classification Search .......... 433/173–175, 433/201.1; 623/17.17
See application file for complete search history.

(56) References Cited

U.S. PATENT DOCUMENTS

| | | | | |
|---|---|---|---|---|
| 3,497,953 A | * | 3/1970 | Weissman ................ | 433/173 |
| 3,628,248 A | * | 12/1971 | Kroder et al. ............ | 433/175 |
| 3,717,932 A | | 2/1973 | Brainin | |
| 3,955,280 A | * | 5/1976 | Sneer ...................... | 433/169 |
| 4,187,608 A | | 2/1980 | Nyce | |
| 5,088,926 A | | 2/1992 | Lang | |
| 5,427,526 A | | 6/1995 | Fernandes | |
| 5,603,616 A | | 2/1997 | Fernandes | |
| 5,766,010 A | * | 6/1998 | Uemura .................. | 433/175 |
| 6,099,313 A | * | 8/2000 | Dorken et al. ........... | 433/175 |
| 6,217,333 B1 | * | 4/2001 | Ercoli .................... | 433/173 |
| 6,743,233 B1 | * | 6/2004 | Baldwin et al. ......... | 606/323 |
| 2002/0155412 A1 | * | 10/2002 | Panzera et al. .......... | 433/223 |
| 2005/0048440 A1 | | 3/2005 | Feng | |

(Continued)

FOREIGN PATENT DOCUMENTS

DE    41 00636 A    7/1992
(Continued)

OTHER PUBLICATIONS

Machine Translation of DE 2004020338 U1. Accessed at EPO website on Jun. 22, 2011.*

(Continued)

*Primary Examiner* — Cris L Rodriguez
*Assistant Examiner* — Edward Moran

(57) ABSTRACT

The invention concerns a non rotation-symmetric but root-analogue or tooth socket-analogue dental implant of the same size and shape as the root of the extracted tooth with macro retentions protruding from the implant surface (107, 113, 116).

Macro retentions (107, 113, 116) are strictly limited to surface areas of the implant in the interdental space next to spongy and thick bone and in case of the last molar, facing the bone at the end of the tooth row. The diameter of the dental implant in transverse direction next to the thin cortical bone buccal and lingual/palatinal is identical to the alveolar bone or preferably stands back to avoid any pressure induced resorption and fracture of the thin cortical bone layer, respectively, at any cost.

31 Claims, 2 Drawing Sheets

U.S. PATENT DOCUMENTS

2007/0264612 A1 * 11/2007 Mount .......................... 433/173

FOREIGN PATENT DOCUMENTS

| DE | 195 13 881 | | 2/1996 |
|---|---|---|---|
| DE | 101 09 118 A | | 9/2002 |
| DE | 2004020338 U1 | * | 6/2005 |
| WO | 88/03391 | | 5/1988 |
| WO | WO 02/45615 A1 | * | 6/2002 |
| WO | WO 03/045268 A1 | * | 6/2003 |
| WO | 2005079696 A1 | | 9/2005 |

OTHER PUBLICATIONS

English Machine Translation for DE 41 00636.
English Machine Translation for DE 195 13 881.
English Machine Translation for DE 101 09 118.
W. Pirker, A. Kocher: Immediate, non-submerged, root-analogue zirconia implant in single tooth replacement. Int J Oral Maxillofac Surg. Mar. 2008; 37(3):293-5. Epub Feb. 12, 2008. PMID: 18272340 Published by Elsevier Ltd.
W. Pirker, A. Kocher: Immediate, non-submerged, root-analogue zirconia implants placed into single-rooted extraction sockets: 2-year follow-up of a clinical study. Int J Oral Maxillofac Surg. Nov. 2009; 38(11):1127-32. Epub Aug. 7, 2009. PMID: 19665354 Published by Elsevier Ltd.
W. Pirker, A. Kocher: True Anatomic Immediate Dental Implant Method a Clinical Case. Implants International Magazine of Oral Implantology 4/4009 OEMUS.
W. Pirker, D. Wiedemann, A. Lidauer, A. A. Kocher : Immediate, singlestage, truly anatomic zirconia implant in lower molar replacement: A case report with 2.5 years follow-up. Int J Oral Maxillofac Surg. Feb. 2011; 40(2):212-6. Epub Sep. 15, 2010. PMID: 20833511 Published by Elsevier Ltd.
W. Pirker, A. Kocher: True anatomical zirconia implants for molar replacement: a case report from an ongoing clinical study with a 2-year follow-up. Oral Surgery 2010; ISSN 1752-2471; Blackwell Munksgaard.
W. Pirker, A. Kocher: True Anatomical Design for Molar Replacement—A Case Report. The International Journal of Periodontics & Restorative Dentistry; vol. 31, No. 6, 2011 Quintessence Publishing Co, Inc.
M.N. Durakbasa, W. Pirker, P.H. Osanna, P. Demircioglu, G. Bas, B. Gültekin,: Application of Advanced Production Metrology for Quality Improvements in Biomedical Engineering—Analysis and Evaluation of Surface Structures of Dental Implants, Joint International MEKO Symposium, 2011, Jena, Germany; Vienna University of Technology, Institute for Production Engineering and Laser Technology, Department of Interchangeable Manufacturing and Industrial Metrology, Karlsplatz 13/3113 1040 Wien, Austria.
Kohal RJ, Hürzeler MB, Mota LF, Klaus G, Caffesse RG, Strub JR; Custom-made root analogue titanium implants placed into extraction sockets. An experimental study in monkeys. C lin Oral Implants Res. Oct. 1997; 8 (5):386-92.
Heydecke G, Kohal R, Gläser R. Optimal esthetics in single-tooth replacement with the Re-Implant system: A case report. International Journal of Prosthodontics Mar.-Apr. 1999;12(2):184-9.

Chahine, Gilbert; Koike, Mari; Okabe, Toru; Smith, Pauline; Kovacevic, Radovan JOM; The Design and Production of Ti-6Al-4V ELI Customized Dental Implants Nov. 2008; 60, 11; ABI/INFORM Complete p. 50.
Chahine Gilbert, Smith Pauline, Kovacevic Radovan, Ajlouni Raed, Ajlouni Khaldoun; Digital Engineering of Bio-Adaptable Dental Implants Engineering—Analysis and Evaluation of Surface Structures of Dental Implants, ISBN 978-953-307-658-4 Publisher InTech, www.intechopen.com, Aug. 2011.
D. Lundgren, H. Rylander, M. Anderssong, C. Johansson, T. Albrektsson, Healing-in of root analogue titanium implants placed in extraction sockets. An experimental study in the beagle dog. Clinical Oral Implants Research vol. 3, Issue 3, pp. 136-144, Sep. 1992.
Kaya Thoma, DMD, Gion F. Pajarola, DMD, Klaus W. Grätz, MD, DMD, Patrick R. Schmidlin, DMD, University of Zürich Center of Dental and Oral Medicine Bioabsorbable root analogue for closure of oroantral communications after tooth extraction: A prospective case cohort study Oral Surgery, Oral Medicin, Oral Pathology, Oral Radiology, Oral Endodontology 2006; 101:558-64.
Kohal R.-J., Klaus, G. Strub, J.R.; Clinical Investigation of a New Dental Immediate Implant System. The ReImplant-System Dtsch Zahnärztl Z. Aug. 2002;57(8):495-7. 2002-2012 Deutscher Ärzte-Verlag; L. N. Schaffrath DigitalMedien GmbH.
EDI Journal (European Journal for Dental Implantologists) ISSN 1862-2879 Issue Jan. 2009 vol. 5 Custom Implant p. 118 Advertisment by Leader Italia S.r.l.Via Aquileja, 49; 20092 Cinisello Balsamo MI Italy www.leaderitalia.it.
Moin DA, Hassan B, Mercelis P, Wismeijer D.; Designing a novel dental root analogue implant using cone beam computed tomography and CAD/CAM technology. Clin Oral Implants Res. Nov. 14, 2011. doi: 10.1111/j.1600-0501.2011.02359.x. PMID: 22092354.
D.R Prithviraj, K.M. Regish, Sharma Deeksha, D.P. Shruthi, Extraction and immediate placement of root analogue zirconia implants: an overview Journal Clinical and Experimental Dentistry, 2011;3(3):e240-5.
Jafar Kolahi, All Aghababagoli, Ahmad Soolari,: Immediate CAD/CAM Custom Fabricated Dental Implants Dent Hypotheses 2010;1:94-98. doi:10.5436/j.dehy. 2010.1.00015 dentalhypotheses. com/index.php/dhj/comment/add/92/0.
K M R, Sharma D, D R P.; An Overview of Immediate Root Analogue Zirconia Implants. International Journal of Oral Implantology, Sep. 9, 2011. PMID: 21905912.
Ghuneim WA.: In situ tooth replica custom implant: rationale, material, and technique. Dr Wael Dental Clinic, Cairo, Egypt. ghuneim@tedata.net.eg J Oral Implantol. 2010;36(6):435-50. Epub Jun. 14, 2010.
Pubmed search 21. Feb. 2012 "root analogue" dental implant: Results 9 http://www.ncbi.nlm.nih.gov/pubmed?term=%22root%20analogue%22%20dental%20implant.
Enterprise europe network provided by EURESEARCH Innovative immediate zirconium dental implants requiring no dental surgery http://swisseen.ch/marketplace/index.php?file=bbs-show.php &bbsref=08%20AT%200102 . . . Feb. 21, 2012.

* cited by examiner

10(a) 10(b) 10(c) 10(d) 10(e) 10(f) 10(g) 10(h)

TOOTH IMPLANT

BACKGROUND OF THE INVENTION

The invention relates to a dental implant with single- or multiple roots, shaped according to the tooth socket or dental root with protruding macro retentions for immediate and delayed tooth replacement.

The established methods of placing dental implants is drilling an implant hole into the bone, inserting the implant into the prepared cavity by tapping and/or screwing. Prefabricated rotation-symmetric implants of varying forms, lengths and diameters require several weeks healing period.

The method with preformed rotationally symmetric implants does not work in cases where primary stability cannot be achieved due to incongruence of the tooth socket and the rotation-symmetric implant. In such cases first a bone healing period is necessary, since the incongruence of the tooth socket to the pre-fabricated rotation-symmetric implant does not allow for primary stability. Therefore it is an advantage to design the dental implant according and congruent to the individual extraction socket.

Prior German Pat. No. DE 101 09 118 A disclosed an individually tailored tooth implant based on an exact impression of the extracted tooth, enlarged about twice the distance of the periodontal ligament, provided with grooves and finally fixed into the bone with press-fit.

Prior WO Pat. No. 88/03391 disclosed a slightly enlarged root analogue press fit technology implant with undercut cavities, distributed equally over the entire root surface.

Another possible technique described in U.S. Pat. No. 5,603,616 A und U.S. Pat. No. 5,427,526 A is a preformed, custom-manufactured, conical, rotation-symmetric, slightly enlarged single root press-fit technology implant reflecting a major portion of the root. The retention elements are uniformly distributed around the implant surface to provide a screw like mechanism when the implant is rotated in the alveolar bone.

Prior German Pat. No. DE 41 00636 A describes a root shaped implant produced by copy milling without any details on the design of the implant surface.

German Pat. No. DE 195 13 881 describes a method enlarging the implant by doubling the width of the periodontal ligament. The whole bone contact section has a number of rectangular, equidistantly spaced, honeycomb-shaped cavities.

U.S. Pat. No. 4,187,608 concerns an exact replica of the extracted tooth, manufactured from porous metal or ceramic through a special sinter process for better adherence and ingrowths of bone matrix.

US Pat. No. US 2005/0048440 A describes an identical replica with special treatments e.g. etching, sandblast, hydroxyapatite coverage and/or drill holes of the implant surface for improved bone adherence.

None of the above mentioned patents using root replicas were clinically sufficiently successful and for that reason all these methods are not established for routine clinical use. Due to the failures of these kinds of dental implants till now rotation-symmetric implants are the state of technique, when immediate tooth replacement with a dental implant is provided.

DESCRIPTION OF THE INVENTION

The aim of the invention is the production of an individual non rotation-symmetric implant by copying the original tooth or an impression of the tooth socket and modifying the implant surface with protruding macro retentions, causing only minimal trauma to the alveolar bone and providing a reproducible and shorter healing period.

For that reason macro retentions must be restricted to special regions to allow for a non-traumatic osseointegration by strictly respecting the strongly variable quantity and/or quality of the surrounding alveolar bone next to the implant surface. It is important to know that the anatomy of the tooth socket consists of thin layers of cortical bone on the inner and outer side of the alveolar ridge and mainly spongy bone between the roots and around the tip of the roots. Cortical bone covering the root is very thin with no or few blood vessel and prone to fracture and pressure induced resorption. In contrast, spongy bone has an excellent blood supply and can be compressed to a certain degree with local fractures causing minimal trauma only, containing a lot of bone morphogenic protein and cells, ensuring a favourable and short healing period.

For that reason the invention describes an implant with protruding macro retention elements strictly restricted to surface areas next to spongy alveolar bone, which can be found regularly in the interdental space between the roots.

The upper and especially the lower jaw withstands stress of macro retentions more easily in regions with spongy bone and in direction of the tooth row that is to say in the interdental space, corresponding to the longitudinal bending force resistance of the bone, especially of the lower jaw. Pressure applied in transverse direction towards the thin cortical bone of the alveolar ridge as induced by macro retentions in this sensitive area, or also generally enlarged dental implant diameters for press-fit technology or inadvertent mechanical force during implant insertion, leads to bone fracture and/or pressure induced unaesthetic resorption of the thin bone layer especially on the outer side of the upper and lower jaws and implant loss.

These macro retentions applied only next to spongy bone have increased and longer lasting primary stability while preventing bone fracture and pressure induced bone resorption of the thin buccal bone layer causing implant failures. Conversely to the technical state of the art, the implant size and shape next to the thin cortical bone fits without any pressure by using the same implant size, or even better slightly reduced implant size, preventing even the slightest pressure to the thin cortical bone layer. Macro retentions must not be added next to the thin cortical bone to avoid fracture and pressure induced bone resorption by all means.

In contrast to the state of technology the implant body is under no circumstances enlarged, neither equally nor unequally over the entire bone-implant surface to avoid bone resorption by pressure to the entire surface at the same time point. This press fit technology with pressure distributed equally over the entire implant surface, leads to implant loss because of the regular conical form of natural roots combined with pressure induced bone resorption all over the implant surface at the same time.

According to the invention the geometry of the extracted tooth or extraction socket respectively are taken by e.g. impressions, laser scanning, computer tomography, magnetic resonance imaging or other techniques and modified with macro retentions with the help of a computer program. Macro retentions are protrusions from the implant surface into the area of the extraction socket of at least 0.08 mm, preferably at least 0.4 mm. The ever essential primary stability is maintained mainly by localized macro retentions, compressing only spongy bone, which are stabilising the implant during the early healing period, preventing that the implant gets lost. After implant insertion pressure induced resorption takes place in the region of the macro retentions caused by remodelling of the adjacent bone. In parallel the bone can heal to the implant surface in all the regions where no macro retentions are preformed directly, without any prior pressure induced resorption always delaying osseointegration. The splitting of different healing mechanisms and healing periods leads to the secondary stability called osseointegration without implant loss and/or unpleasant bone resorption.

The aim of the present invention is the production of a dental implant which is not only a exact replica of the root or extraction socket to get maximal implant and bone contact but a dental implant that carries also special macro retentions strictly respecting the anatomy e.g. the bone quality and quantity and the different capabilities to withstand load bearing forces of macro retentions maintaining essential primary stability for osseointegration and preventing bone resorption and even fracture of the thin cortical bone layers.

Macro retentions are essential to keep the conical root analogue implant safely in place during the healing period at least for six to eight weeks by localized compression of exclusively the spongy bone to promote rapid and secure osseointegration on all areas with strain less fit, where no prior pressure induced resorption takes place. In all regions of pressure, osseointegration is delayed, due to prior pressure induced bone resorption.

Contrary to the macro retentions, micro retentions cover the entire surface of the root replica adjacent to bone. Micro retentions are created by sandblast of the preferred implant material $ZrO_2$ (Y-TZP Tetragonal Zirkonia Polycristal, Yttrium stabilized) and have a surface roughness of 40 μm to 70 μm. The surface is therefore treated with pulsed particular blast e.g. Aluminiumoxid- or Zirconoxid particles blasts with 1 to 3 bar pressure in the size of approximately 250 μm between 0.1 to 0.5 seconds per blasted area, in the non sintered material, creating an average roughness of 50 μm to 70 μm. The implant is subsequently sintered.

The number of macro retentions depends on the anatomical circumstances e.g. position of the root (upper-, lower jaw, front-, premolar-, or molar region, single-, or multi rooted, and length of the root). In single rooted teeth between 2 and 8, in most cases 4 macro retentions can be designed. The height of these retentions, that is to say the highest elevation above the root surface is minimally 0.08 mm or better 0.1 mm and preferably at least more than 0.2 mm, and preferably greater than 0.4 mm. When applying macro retentions with different heights in one implant, the height can increase starting from the first macro retention next to the apex following the conical shape of the root towards the crown, in order to avoid any unnecessary damage to the tooth socket at the time point of insertion. No macro retentions are placed on the root next to the bony margin (implant shoulder) in order to protect the thin interdental spongy bone preventing unaesthetic recession of the papilla. On the contrary, the implant diameter is preferably reduced by 0.05 mm to 1 mm, if necessary by 1.5 mm to avoid pressure induced resorption and fracture of the thin cortical bone layer, respectively, at any cost. In general, macro retentions can be larger in cases with more spongy bone and/or if the spongy bone is less dense.

In an alternative embodiment of the invention with regard to single rooted teeth preferably longish macro retentions are created in longitudinal direction in the bony interdental root areas preferably next to the thicker palatinal/lingual bony regions to serve as guidance. This will avoid application of pressure to the thin cortical bone buccal, leading to pressure-induced bone resorption and even fracture and dislocation in buccal direction of the single rooted implant during insertion. In multirooted teeth the anatomy averts the possibility of dislocation during insertion.

Another embodiment of the invention is shortening of the implant at the apex, preferably by 0.3 mm to 1 mm in order to avoid compression of the bone around the apex of the implant, leading to pressure in extraction direction on the implant later on.

DESCRIPTION OF THE DRAWINGS

Figure 1:
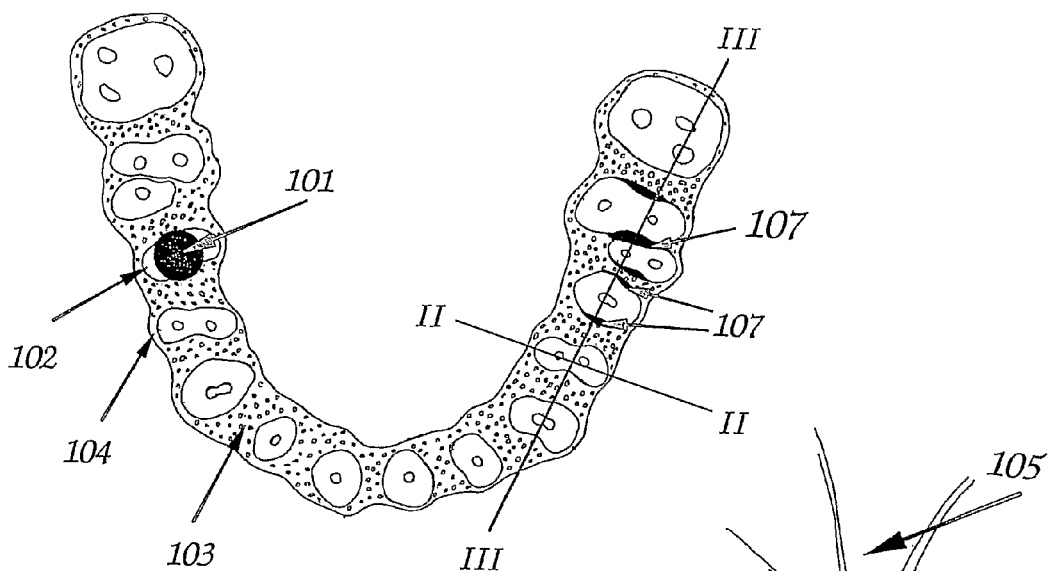
FIG. 1 axial cross section of the human upper jaw in the middle of the roots (according to an axial computed tomography scan)

FIG. 1 illustrates a human upper jaw, the outer side is referred to as buccal, the inner side as palatinal. 101 indicates a cylindrical implant corresponding to the state of the technology, leading to clearly visible gaps and incongruences marked as 102 causing bone resorption and a lack of primary stability.

The bone jaw is not uniform, but consists of compact bone marked with 104 and spongy bone marked as 103. The spongy bone is extended in the interdental space and around the lower parts of the roots, especially in the lower jaw. In contrast, the compact bone covers as a thin, non compressible and non load bearing, cortical layer the upper part of the root palatinal, lingual, extra thin buccal and labial.

Figure 2:
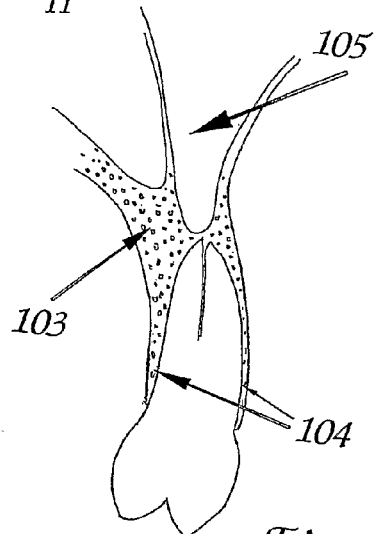
FIG. 2 section of a tooth in the upper jaw in section II-II according to FIG. 1

FIG. 2 illustrates a cross section along the line of intersection II-II of FIG. 1 through a tooth in bucco-palatinal direction, clearly showing the very thin cortical bone layer covering the outer (buccal) face of the root.

Figure 3:
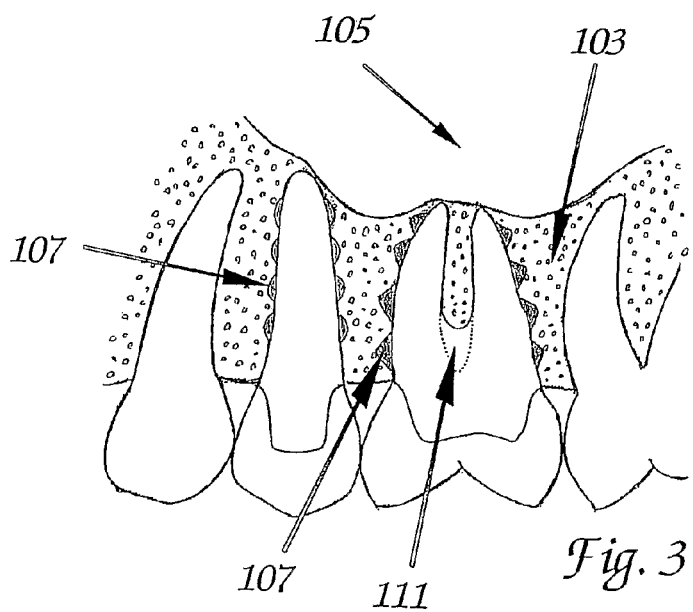
FIG. 3 section of a tooth in the upper jaw in section III-III according to FIG. 1

FIG. 3 shows a cross section in the row of teeth according to intersection line III-III of FIG. 1. Spongy bone (103) extends in the interdental space. The invention describes macro retentions (107) in the area of spongy bone, preferably in the interdental space, where enough spongy bone is always present. In order to reach primary stability, selective macro retentions in spongy bone are sufficient. The areas kept free of macro retentions and preferably of implant diameter reduction according to the invention are marked in the figures as 110. 105 denotes the maxillary sinus.

Figure 4:
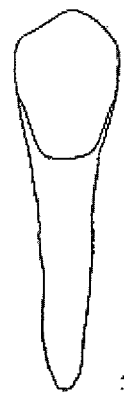
FIG. 4 a premolar—buccal view
Figure 5:
FIG. 5 root-analogue implant in accordance with the invention with crown stump and macro retention—buccal view FIG. 6 premolar of FIG. 4—interdental view FIG. 7 implant according to FIG. 5 with macro retentions in the interdental space—interdental view FIG. 8 cylindrical titan-implant corresponding to the state of the technology FIG. 9 some examples for the arrangement of macro retentions on the implant FIG. 10(*a*) cross section schematic of an embodiment of the macro retentions FIG. 10(*b*) cross section schematic of another embodiment of the macro retentions FIG. 10(*c*) cross section schematic of another embodiment of the macro retentions FIG. 10(*d*) cross section schematic of another embodiment of the macro retentions FIG. 10(*e*) cross section schematic of another embodiment of the macro retentions FIG. 10(*f*) cross section schematic of another embodiment of the macro retentions FIG. 10(*g*) cross section schematic of another embodiment of the macro retentions FIG. 10(*h*) cross section schematic of another embodiment of the macro retentions FIG. 11 an embodiment of the invention with extended root and FIG. 12 an embodiment of the invention with discrete macro retentions.
Figure 6:
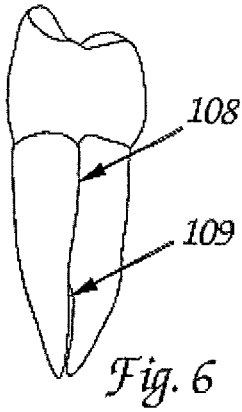

FIG. 4 shows the buccal view of a human tooth and FIG. 5 a corresponding implant with a crown stump (106) and macro retentions (107) according to the invention. FIG. 6 shows an interdental view of the same premolar. The retraction (108) between the roots and the split of the root in two roots in the apical third (109) is illustrated in FIG. 6.

Figure 7:
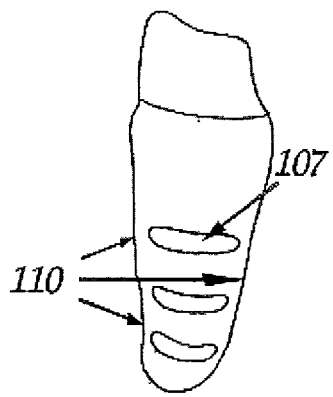

FIG. 7 illustrates a corresponding implant according to the invention. This view shows clearly macro retentions in the interdental space only. The areas kept free of macro retentions and preferably of implant diameter reduction according to the invention are marked in the figures as 110.

Figure 8:

In comparison to the embodiment according to the invention FIG. 8 shows an implant according to the state of the technology, which is rotation symmetric, with a screw like winding for macro retentions.

Figure 9:
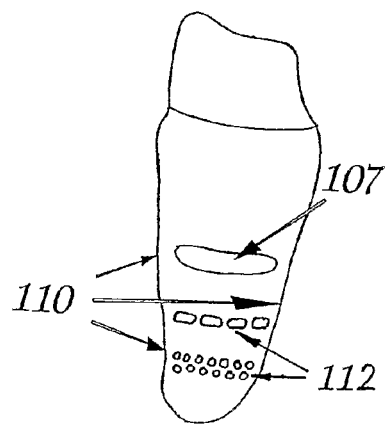
Figure 12:
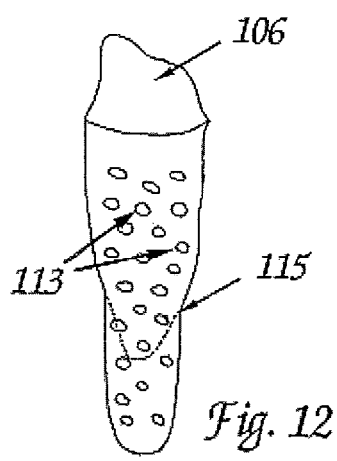
Figure 10:
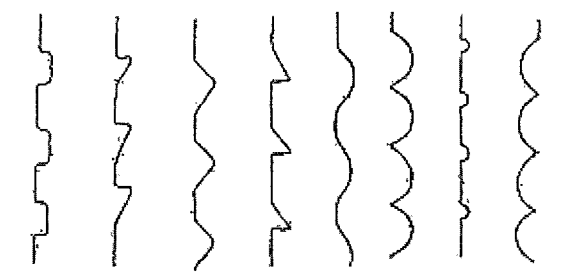

The form of macro retentions (107) can be multifaceted as shown in FIGS. 10(*a*)-10(*h*). The depicted profiles can also be used in mirror image except for 10(*b*) and 10(*g*). In principal any kind of protrusion is eligible e.g. undulated, spikes, teeth, rectangular or rounded, triangular or reticular. These macro retentions can be of one piece with the implant or added onto the implant, in this case preferably by cementing or gluing. Macro retentions can be continuous (107) or interrupted (FIG. 9, 112). Interrupted macro retentions running in circumferential direction can be in line, shifted or randomly distributed (FIG. 12, 113). In at least one embodiment, the macro retentions are oriented at right angles to the longitudinal axis of the extracted tooth.

The herein described invention can be adapted by means of computer aided design and computer aided manufacturing with an already existing or slightly modified software in a way that missing parts of the root (e.g. status post root resection) can be restored, so that the original space in the tooth socket is filled. By the same token tooth anomalies can be corrected and the root form adapted to facilitate implantation: super numerous and significantly curved roots can be partially or completely omitted or straightened. Bifurcated roots with a small bony septum can be partially or completely fused (FIG. 3, 111) after resection of parts or the complete septum, preferably with an impression or computer aided measurement.

The connection of the implant to the crown can have various forms, as are known from the state of the technology, e.g. screw thread, inner- or outer cone, crown stump and glued or screwed connections. According to the state of technology the connection between the implant body and the crown can be in height, above or below the gingiva. Implantation in the level or below the gingival is preferable in cases of poor bone quality or in case of infection and allows for osseointegration without intense functional load. On the other hand, in cases with good bone quality the crown can be fixed to the implant immediately after implant insertion according to early implant loading protocols.

The implant can be manufactured from any material known from the state of technology, preferably ZrO2. It has to be biocompatible and non resorbable. The surface of the implant in the bone connection area has to be roughened according to the state of technology by sandblast, etching and/or coated with hydroxyapatite (roughness corresponds to micro retentions). Growth factors and/or stem cells can also be applied to the implant in order to enhance growth of bone and gingival respectively. While there has been described what is believed to be the preferred embodiment of the present invention, further modification of the surface of the implant or regarding crown technology may be made thereto without departing from the spirit of the invention.

Figure 11:
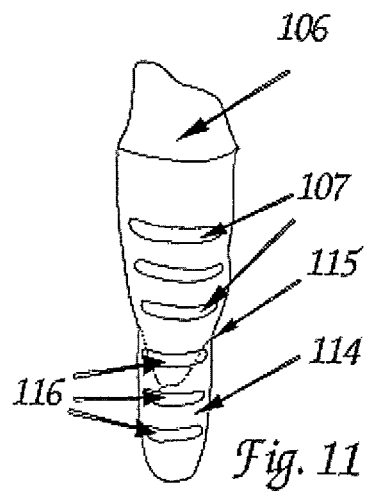

An important aspect of the invention is the possibility to deepen the tooth socket in cases with periodontal lesions or short roots in order to lengthen the implant in longitudinal direction in the axis of the tooth. This leads to an increase of the surface and improved stability (FIG. 11, 12). In these instances the dental implant consists of a root replica and a cylindrical part (114) extending the apex of the implant corresponding to the drilled hole extending the natural tooth socket in the apex area.

Further macro retentions can be added to the extended part of the implant (FIG. 11, 12) Macro retentions can be distributed around on the cylindrical extension part of the implant, as described above, according to the bone quality and quantity. The cross section of the root extension can also be oval or have any other form, because the implant is never screwed but tapped into place.

Another aspect of the invention is the prevention of gingival and/or bony pockets in multi rooted teeth with parodontitis. In these cases the bifurcation or trifurcation can be extended towards the apical direction after resection of adequate septal bone (FIG. 3, 111).

Another possibility is the modification of the tooth socket depending on the bone quality and quantity prior to manufacturing of the implant and creating corresponding macro retentions on the implant body.

What is claimed as new and is desired to be secured by the patent:

1. A dental implant comprising;
    an implant body having a custom made root portion adapted according to a tooth socket of a specific patent for implanting into the jaw, and a crown connection portion, attached to the coronal end of said root portion, for connecting to a crown;
    wherein, said custom made root portion is an analogue of an extracted tooth root or extraction socket, having a shape that is a copy of the shape of said tooth root or extraction socket, so that the extraction socket is almost completely filled by the custom made root portion when implanted;
    a plurality of protruding macro retentions connected to or formed integral with said custom root portion, said macro retentions located on said custom root portion and below an implant shoulder, so that when implanted said macro retentions are adapted to only protrude into thick, spongy bone, regularly found in the inter dental space, and in the case of terminal teeth, toward the bone at the posterior end of the tooth row, thereby causing pressure induced resorption only in regions of spongy bone and therefore securing primary stability of the implant; and
    wherein labial and lingual surfaces of said custom root portion and areas above said implant shoulder, adapted to contact thin cortical bone when implanted, are free of macro retentions, and are adapted to substantially conform to the extraction socket or stand slightly behind the surface of the tooth socket, therefore causing no pressure induced resorption or even fracture, such that by leaving a very small gap, fracture of the thin bone layer does not occur.

2. The dental implant of claim 1, wherein said macro retentions are oriented at right angles to the longitudinal axis of the root portion.

3. The dental implant of claim 1, wherein said macro retentions have an undulated, rectangular or triangular profile.

4. The dental implant of claim 1, wherein said macro retentions are formed as multiple straight or waved protrusions.

5. The dental implant of claim 1, wherein said custom root portion has at least one macro retention extending from the root portion that will extend into an inter dental space adjacent to a palatinal/lingual portion of the alveolar bone.

6. The dental implant of claim 1, wherein said macro retentions extend a distance of at least 0.08 mm from a surface of the root portion into the alveolar bone.

7. The dental implant of claim 1, wherein said macro retentions extend a distance of at least 0.2 mm from a surface of the root portion into the alveolar bone.

8. The dental implant of claim 1, wherein said macro retentions extend a distance of at least 0.4 mm from a surface of the root portion into the alveolar bone.

9. The dental implant of claim 1, wherein there are at least two of said macro retentions spaced vertically apart.

10. The dental implant of claim 9, wherein at least two of said macro retentions extend different distances into the bone.

11. The dental implant of claim 10, wherein said distance the macro retentions extend into the bone increases in a direction from a bottom portion of the root portion towards a top portion of the root portion.

12. The dental implant of claim 1, wherein said implant body comprises zirconium oxide and a surface of the root portion has a roughness of 50 μm to 70 μm prior to the implant body being sintered.

13. The dental implant of claim 1, wherein said implant body further comprises a substantially cylindrical extension portion extending from the apical end of the root portion into the extraction socket.

14. The dental implant of claim 13, wherein at least on macro retention is connected to the extension portion.

15. The dental implant of claim 1, wherein said root portion has a shape that copies a shape of a multirooted tooth.

16. The dental implant of claim 1, wherein a transverse diameter of the root portion is 0.05 mm to 1.0 mm smaller than the diameter of the root of the extracted tooth in portions of the root portion adapted to be adjacent buccal and palatinal/lingual bone areas of the tooth socket.

17. A method of forming a custom dental implant, comprising;
measuring the geometry of a tooth root or tooth socket;
forming a custom dental implant comprising; an implant body having a custom made root portion adapted according to a tooth socket of a specific patent for implanting into the jaw, and a crown connection portion, attached to the coronal end of said root portion, for connecting to a crown;
wherein, said custom made root portion is an analogue of an extracted tooth root or extraction socket, having a shape that is a copy of the shape of said tooth root or extraction socket, so that the extraction socket is almost completely filled by the custom made root portion when implanted;
a plurality of protruding macro retentions connected to or formed integral with said custom root portion, said macro retentions located on said custom root portion and below an implant shoulder, so that when implanted said macro retentions are adapted to only protrude into thick, spongy bone, regularly found in the inter dental space, and in the case of terminal teeth, toward the bone at the posterior end of the tooth row, thereby causing pressure induced resorption only in regions of spongy bone and therefore securing primary stability of the implant; and
wherein labial and lingual surfaces of said custom root portion and areas above said implant shoulder, adapted to contact thin cortical bone when implanted, are free of macro retentions, and are adapted to substantially conform to the extraction socket or stand slightly behind the surface of the tooth socket, therefore causing no pressure induced resorption or even fracture, such that by leaving a very small gap, fracture of the thin bone layer does not occur;
treating the surface of the unsintered root portion with a pulsed particular blast of aluminum oxide or zirconium oxide particles with a size of about 250 microns at 1 to 3 bar pressure for between 0.1 to 0.5 seconds per blasted area to create an average surface roughness of 50 microns to 70 microns; and
sintering implant after the surface treatment.

18. The method of claim 17, wherein said macro retentions are oriented at right angles to the longitudinal axis of the root portion.

19. The method of claim 17, wherein said macro retentions have an undulated, rectangular or triangular profile.

20. The method of claim 17, wherein said macro retentions are formed as multiple straight or waved protrusions.

21. The method of claim 17, wherein said custom root portion has at least one macro retention extending from the root portion that will extend into an inter dental space adjacent to a palatinal/lingual portion of the alveolar bone.

22. The method of claim 17, wherein said macro retentions extend a distance of at least 0.08 mm from a surface of the root portion into the alveolar bone.

23. The method of claim 17, wherein said macro retentions extend a distance of at least 0.2 mm from a surface of the root portion into the alveolar bone.

24. The method of claim 17, wherein said macro retentions extend a distance of at least 0.4 mm from a surface of the root portion into the alveolar bone.

25. The method of claim 17, wherein there are at least two of said macro retentions spaced vertically apart.

26. The method of claim 25, wherein at least two of said macro retentions extend different distances into the bone.

27. The method of claim 26, wherein said distance the macro retentions extend into the bone increases in a direction from a bottom portion of the root portion towards a top portion of the root portion.

28. The method of claim 17, wherein said implant body further comprises a substantially cylindrical extension portion extending from the apical end of the root portion into the extraction socket.

29. The method of claim 28, wherein at least on macro retention is connected to the extension portion.

30. The method of claim 17, wherein said root portion has a shape that copies a shape of a multirooted tooth.

31. The method of claim 17, wherein a transverse diameter of the root portion is 0.05 mm to 1.0 mm smaller than the diameter of the root of the extracted tooth in portions of the root portion adapted to be adjacent buccal and palatinal/lingual bone areas of the tooth socket.

* * * * *

UNITED STATES PATENT AND TRADEMARK OFFICE
CERTIFICATE OF CORRECTION

PATENT NO.        : 8,287,279 B2  
APPLICATION NO.   : 12/089268  
DATED             : October 16, 2012  
INVENTOR(S)       : Wolfgang Pirker Page 1 of 1

It is certified that error appears in the above-identified patent and that said Letters Patent is hereby corrected as shown below:

PRESENT VERSION WITH TYPOGRAPHICAL MISTAKES:
53. (new) A dental implant comprising;
an implant body having a custom made root portion adapted according to a tooth socket of a specific patent for implanting into the jaw, and a crown connection portion, attached to the coronal end of said root portion, for connecting to a crown;

NEW VERSION;
53. (new) A dental implant comprising;
an implant body having a custom made root portion adapted according to a tooth socket of a specific patient for implanting into the jaw, and a crown connection portion, attached to the coronal end of said root portion, for connecting to a crown;

PRESENT VERSION WITH TYPOGRAPHICAL MISTAKES:
69. (new) A method of forming a custom dental implant, comprising;
measuring the geometry of a tooth root or tooth socket;
forming a custom dental implant comprising; an implant body having a custom made root portion adapted according to a tooth socket of a specific patent for implanting into the jaw, and a crown connection portion, attached to the coronal end of said root portion, for connecting to a crown;

NEW VERSION:
69. (new) A method of forming a custom dental implant, comprising;
measuring the geometry of a tooth root or tooth socket;
forming a custom dental implant comprising; an implant body having a custom made root portion adapted according to a tooth socket of a specific patient for implanting into the jaw, and a crown connection portion, attached to the coronal end of said root portion, for connecting to a crown;

Signed and Sealed this
Twentieth Day of November, 2012

David J. Kappos
*Director of the United States Patent and Trademark Office*

UNITED STATES PATENT AND TRADEMARK OFFICE
CERTIFICATE OF CORRECTION

PATENT NO.        : 8,287,279 B2
APPLICATION NO.   : 12/089268
DATED             : October 16, 2012
INVENTOR(S)       : Wolfgang Pirker Page 1 of 1

It is certified that error appears in the above-identified patent and that said Letters Patent is hereby corrected as shown below:

Title page, Item (75) Inventor: "Wofgang Pirker" should read --Wolfgang Pirker--.

Column 6, lines 40-45 (Claim 1, lines 1-6)
"1. A dental implant comprising;
an implant body having a custom made root portion adapted according to a tooth socket of a specific patent for implanting into the jaw, and a crown connection portion, attached to the coronal end of said root portion, for connecting to a crown;".

should read
--1. A dental implant comprising;
an implant body having a custom made root portion adapted according to a tooth socket of a specific patient for implanting into the jaw, and a crown connection portion, attached to the coronal end of said root portion, for connecting to a crown;--.

Column 6, lines 50-58 (Claim 17, lines 1-9)
"17. A method of forming a custom dental implant, comprising;
measuring the geometry of a tooth root or tooth socket;
forming a custom dental implant comprising; an implant body having a custom made root portion adapted according to a tooth socket of a specific patent for implanting into the jaw, and a crown connection portion, attached to the coronal end of said root portion, for connecting to a crown;".

should read
--17. A method of forming a custom dental implant, comprising;
measuring the geometry of a tooth root or tooth socket;
forming a custom dental implant comprising; an implant body having a custom made root portion adapted according to a tooth socket of a specific patient for implanting into the jaw, and a crown connection portion, attached to the coronal end of said root portion, for connecting to a crown;--.

This certificate supersedes the Certificate of Correction issued November 20, 2012.

Signed and Sealed this
Eighth Day of January, 2013

David J. Kappos
*Director of the United States Patent and Trademark Office*